US00RE39056E

(19) United States
(12) Reissued Patent
Bakshi et al.

(10) Patent Number: US RE39,056 E
(45) Date of Reissued Patent: Apr. 4, 2006

(54) 4-AZASTEROIDS FOR TREATMENT OF HYPERANDROGENIC CONDITIONS

(75) Inventors: Raman K. Bakshi, Edison, NJ (US); Soumya P. Sahoo, Old Bridge, NJ (US); Richard L. Tolman, Los Altos, CA (US)

(73) Assignee: Merck & Co, Inc., Rahway, NJ (US)

(21) Appl. No.: 10/020,740

(22) PCT Filed: Sep. 11, 1996

(86) PCT No.: PCT/US96/14564

§ 371 (c)(1),
(2), (4) Date: Mar. 11, 1998

(87) PCT Pub. No.: WO97/10217

PCT Pub. Date: Mar. 20, 1997

Related U.S. Patent Documents

Reissue of:
(64) Patent No.: 6,001,844
Issued: Dec. 14, 1999
Appl. No.: 09/029,926
Filed: Mar. 11, 1998

U.S. Applications:
(60) Provisional application No. 60/003,826, filed on Sep. 15, 1995.

(51) Int. Cl.

| | |
|---|---|
| ***A61K 31/435*** | (2006.01) |
| ***A61K 31/44*** | (2006.01) |
| ***A61P 5/28*** | (2006.01) |
| ***C07D 221/02*** | (2006.01) |
| ***C07D 221/18*** | (2006.01) |

(52) U.S. Cl. ..... 514/284; 514/255.05; 514/256; 514/26.222; 514/269; 514/272; 514/274; 514/275; 544/265; 544/266; 544/268; 544/276; 544/277; 544/301; 544/311; 544/312; 544/316; 544/317; 544/319; 544/320; 544/322; 544/323; 544/329; 544/332; 544/334; 544/335; 544/336; 544/408; 544/409; 546/77

(58) Field of Classification Search ..... 514/255.05, 514/256, 263.22, 269, 272, 274, 275, 284; 544/265, 266, 268, 276, 277, 301, 311, 312, 544/316, 317, 319, 320, 322, 323, 329, 332, 544/334, 335, 336, 408, 409; 546/77
See application file for complete search history.

(56) References Cited

U.S. PATENT DOCUMENTS

| | | | | | |
|---|---|---|---|---|---|
| 4,191,759 | A | * | 3/1980 | Johnston | 424/242 |
| 4,377,584 | A | * | 3/1983 | Rasmusson et al. | 424/258 |
| 4,760,071 | A | * | 7/1988 | Rasmusson et al. | 514/284 |
| 5,084,574 | A | | 1/1992 | Bhattacharya et al. | 546/77 |
| 5,116,983 | A | * | 5/1992 | Bhattacharya | 546/14 |
| 5,151,429 | A | * | 9/1992 | Rasmusson | 514/284 |
| 5,302,621 | A | * | 4/1994 | Kojima et al. | 514/284 |
| 5,304,562 | A | * | 4/1994 | Biollaz | 514/284 |
| 5,547,957 | A | | 8/1996 | Gormley et al. | 514/284 |
| 5,565,467 | A | * | 10/1996 | Batchelor et al. | 514/284 |
| 5,693,809 | A | | 12/1997 | Durette et al. | 546/77 |
| 5,693,810 | A | | 12/1997 | Rasmusson et al. | 546/77 |
| 5,696,266 | A | | 12/1997 | Humphrey et al. | 546/77 |
| 5,817,802 | A | | 10/1998 | Humphrey et al. | 540/77 |
| 5,872,126 | A | | 2/1999 | Cukierski et al. | 514/284 |
| 5,998,427 | A | * | 12/1999 | Batchelor et al. | 514/284 |
| 6,121,449 | A | | 9/2000 | Panzeri et al. | 546/77 |
| 6,645,974 | B1 | * | 11/2003 | Hutchinson et al. | 514/284 |

FOREIGN PATENT DOCUMENTS

| | | | |
|---|---|---|---|
| EP | 0 004 949 B1 | | 4/1979 |
| EP | 0 004 949 A1 | | 4/1979 |
| EP | 0 655 459 A2 | | 11/1990 |
| EP | 0 484 094 | * | 6/1992 |
| EP | 0 538 192 | * | 4/1993 |
| WO | WO 92/16213 | * | 10/1992 |
| WO | WO 94/07861 | * | 4/1994 |
| WO | WO 94/11385 | | 5/1994 |
| WO | WO 94/15602 | | 7/1994 |
| WO | WO 95/07926 | * | 3/1995 |
| WO | WO 95/07927 | * | 3/1995 |
| WO | WO 97/11702 | | 4/1997 |

OTHER PUBLICATIONS

Bakshi, R.K., et al., 4–aza–3–oxo–5a–androst–1–ene–17b–N–aryl–carboxamides as dual inhibitors of human type 1 and type 2 steroid 5a–reductases. J. Med. Chem. 38 (1995), pp. 3189–3192.*

(Continued)

*Primary Examiner*—Brenda Coleman
(74) *Attorney, Agent, or Firm*—Patricia A. Shatynski; Mark R. Daniel

(57) ABSTRACT

Compounds of structural Formula (I)

(I)

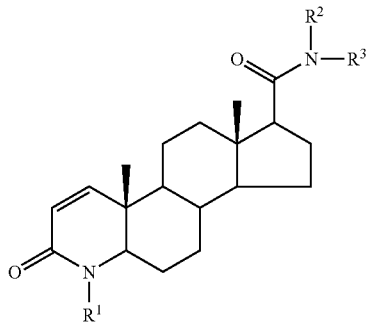

and pharmacologically acceptable salts and esters thereof possess 5α-reductase inhibitory activity. These compounds inhibit 5α-reductase type 1 and type 2. The compounds of structural Formula I are useful in the systemic, including oral, and parenteral, including topical, treatment and prevention of hyperandrogenic conditions including prostatic carcinoma, benign prostatic hyperplasia, acne vulgaris, seborrhea, androgenic alopecia (also called androgenetic alopecia) which includes male- and female-pattern baldness, female hirsutism, and prostatitis. A class of compounds of the present invention are also potent antiandrogens. The present invention also relates to novel compositions containing such compounds, methods of their use and methods of their manufacture.

2 Claims, No Drawings

OTHER PUBLICATIONS

Tolman et al., "4–Methyl–3–oxo–4–aza–5alpha–androst–1–en17beta–N–aryl–carboxamides: An approach to combined androgen blockage"; Mar. 1997 issue of J. Steroid Biochem & Molec. Bio. vol. 60, No. 5–6 pp. 303–309.*

Andriole et al., "Treatment with Finasteride Following Radical Prostatectormy for Prostate Cancer", Urology 45(3): 491–497 (1995).

Tsukamoto et al., "Chemoprevention of Rat Prostate Carcinogenesis by Use of Finasteride or Casodex", 87 J. Nat'l Cancer Inst., pp. 842–843 (1995).

Tolman et al., 5th Int'l Congress Hormones & Cancer Program and Abstract, Quebec City, Sep. 16–20, 1995, p. 92, Abstract 48, 4–methyl–4–azateroid 17beta(N–aryl substituted)carboxamides: Potent antiandrogenic activity with 5a–reductase inhibition.

Bologna et al, "Antiandrogens and 5–alpha Reductase Inhibition of the Proliferation Rate in PC3 and DU145 Human Prostatic Cancer Cell Lines", 51(6) Curr. Ther. Res., pp. 799–813 (1992).

Denis, Commentary on maximal androgen blockade in prostate cancer: A theory to put into practice. Prostate 27 (1995), pp. 223–240.

Bakshi et al., ACS Division of Medicinal Chemistry, 209th ACS Nat'l meeting Anaheim, CA, Apr. 2–6, 1995, Abstract No. 011, N–Phenyl–3–oxo–4–aza–5alpha–androst–1–en–17beta–carboxamides as inhibitors of both human type 1 and type 2 5alpha–redutases.

Rasmusson et al., J. Med. Chem., vol. 29, pp. 2298–2315 (1986), "Azasteroids: Structure–activity relationships for inhibition of 5alpha–reductase and of androgen receptor binding."

Liang et al., Endrocrinology, vol. 117, pp. 571–579 (1985), "Species differences in prostatic steroid 5alpha–reductases of rat, dog, and human".

Bakshi, R.K., et al., "4–Aza–3–oxo–5a–androst–1–ene–17b–N–aryl–carboxamides as Dual Inhibitors of Human Type 1 and Type 2 Steroid 5a–Reductases. Dramatic Effect of N–Aryl Substituents on Type 1 and Type 2 5a–Reductase Inhibitory Potency.", J. Med. Chem., vol. 38, No. 17, 1995.

Bakshi, et al., Additions and Corrections, J. of Med. Chem., vol. 39, No. 5, p. 1192, 1996.

Mellin, T.N., et al., "Azateroids as Inhibitors of Testosterone 5a–Reductase In Mammalian Skin", J. of Steroid Biochem. and Molec. Bio., vol. 44, No. 2, pp. 121–131, 1993.

Rasmusson, G.H., et al., "Azasteroids as Inhibitors of Rat Prostatic 5a–Reductase", J. of Med. Chem., vol. 27, No. 12, pp. 1690–1701, 1984.

Zheng, Jinhong, et al., Chem. Abs., vol. 122, No. 25, 1995.

Kurata, H., et al., "Synthesis and Testosterone 5a–Reductase–Inhibitory Activity of 4–Aza–5a–androstane–17–caboxamide Compound with an Aromatic Moiety in the C–17 Carbamoyl Group", Chem. Pharm. Bull. vol. 44(1), pp. 115–121 (1996).

* cited by examiner

4-AZASTEROIDS FOR TREATMENT OF HYPERANDROGENIC CONDITIONS

Matter enclosed in heavy brackets [ ] appears in the original patent but forms no part of this reissue specification; matter printed in italics indicates the additions made by reissue.

CROSS REFERENCE TO RELATED APPLICATIONS

The present application is the national phase application under 35 U.S.C. 0371 of PCT application Ser. No. PCT/US96/14564, filed Sep. 11, 1996, based on provisional application 60/003,826, filed Sep. 15, 1995.

BACKGROUND OF THE INVENTION

The present invention relates to novel compounds, novel compositions, methods of their use and methods of their manufacture where such compounds are generally pharmacologically useful as agents in therapies for diseases relating to hyperandrogenic stimulation, particularly caused by excessive accumulation of testosterone ("T") dihydrotestosterone ("DHT") and similar androgenic hormones in the metabolic system.

The novel compounds of the present invention are especially useful in the prevention and treatment of prostatic carcinoma, and they may also be useful in the treatment and prevention of other hyperandrogenic diseases such as acne vulgaris, seborrhea, female hirsutism, also called androgenic alopecia which includes female and male pattern baldness, and benign prostatic hyperplasia.

The compounds of the present invention are 3-oxo-4-azasteroids, particularly 17-substituted, 4-aza-5α-androstan-3-one derivatives.

Finasteride, (17β-(N-tert-butylcarbamoyl)-3-oxo-4-aza-5α-androst-1-ene-3-one) as shown below, is a potent inhibitor of the human prostate enzyme.

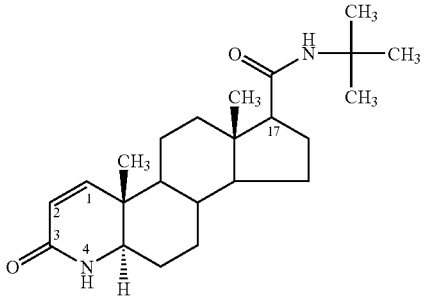

finasteride

Under the trade name PROSCAR®, finasteride is known to be useful in the treatment of hyperandrogenic conditions; see e.g. U.S. Pat. No. 4,760,071. Finasteride is currently prescribed for the treatment of benign prostatic hyperplasia (BPH), a condition afflicting to some degree the majority of men over age 55. Finasteride's utility in the treatment of androgenic alopecia and prostatic carcinoma is also disclosed in the following documents: EP 0 285,382, published Oct. 5, 1988; EP 0 285,383, published Oct. 5, 1988; Canadian Patent no. 1,302,277; and Canadian Patent no. 1,302,276.

Finasteride is a 5α-reductase inhibitor, The enzyme 5α-reductase catalyzes the reduction of testosterone to the more potent androgen, dihydrotestosterone, as shown below:

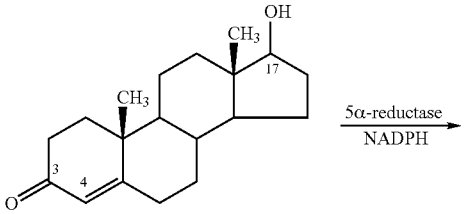

testosterone

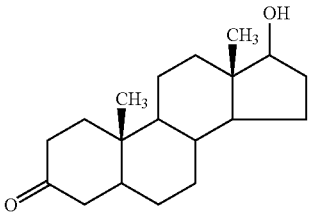

dihydrotestosterone

The principal mediator of androgenic activity in some target organs, e.g. the prostate, is 5α-dihydrotestosterone ("DHT"), formed locally in the target organ by the action of testosterone-5α-reductase. Inhibitors of testosterone-5α-reductase prevent or lessen symptoms of hyperandrogenic stimulation in these organs.

There are two isozymes of 5α-reductase in humans. One isozyme (type 1) predominates in sebacious glands of facial and skin tissue and is relatively insensitive to finasterides, the other (type 2) predominates in the prostate and is potently inhibited by finasteride. European patent publication EP 0 547 691 discloses 17-substituted 4-aza-5α-androstan-3-one derivatives useful in the treatment of prostatic carcinoma.

European Patent Publication 0 484 094 discloses 4-azasteroid compounds with 17-aryl carboxamide substitutions.

Other attempts to provide a chemotherapeutic agent to counter the desirable results of hyperandrogenicity led to the discovery of steroidal antiandrogens such as: hydroxyflutamide (the active form of flutamide), and Casodex™ (the trademark for ICI 176,334 from Imperial Chemical Industries PLC).

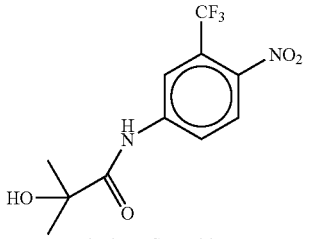

hydroxyflutamide

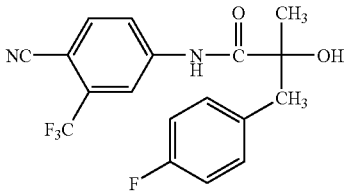

Casodex

For the treatment of advanced prostatic carcinoma therapy has included castration by surgery (orchidectomy) or by using an LHRH agonist.

There remains a need for an agent which approaches the treatment of hyperandrosgenic diseases by inhibiting both the isozymes of 5α-reductase. The present invention provides for such compounds.

SUMMARY OF THE INVENTION

The novel compounds of the present invention are those of structural Formula (I)

(I)

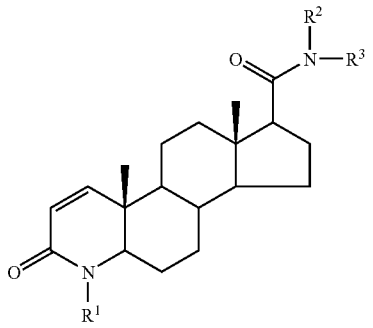

and a pharmaceutically acceptable salts and esters thereof which are potent antiandrogens. These compounds inhibit 5α-reductase type 1 and 2. The compounds of structural Formula I are useful in the systemic, including oral, and parenteral, including topical, treatment and prevention of hyperandrogenic conditions including prostatic carcinoma, benign prostatic hyperplasia, acne vulgaris, seborrhea, androgenic alopecia (also called androgenic alopecia) which includes male- and female-pattern baldness, female hirsutism, and prostatitis.

Therefore, it is an object of the present invention to provide compounds which exhibit 5α-reductase type 1 and type 2 inhibitory activity. It is a further object of the present invention to provide a class of compounds which exhibit androgen receptor antagonistic and 5α-reductase inhibitory activity. It is an additional object of this invention to provide methods of using the compounds of Formula I for the treatment of hyperandrogenic conditions such as acne vulgaris, seborrhea, androgenic alopecia, male pattern baldness, female hirsutism, benisgn prostatic hyperplasia, and the prevention and treatment of prostatic carcinomas, as well as the treatment of prostatitis. It is a further object of this invention to provide pharmaceutical compositions for the compounds of formula I. Another object of this invention is to provide compounds of formula I in combination with other active agents, for example a 5α-reductase type 2 inhibitor, such as finasteride, or a potassium channel operator, such as minioxidil, or a retionic acid or a derivative thereof, or an α1- or $\alpha 1_{\alpha}$-adrenergic receptor antagonist, or combinations of such other active agents with a compound of Formula I, wherein such combinations would be useful in one or more of the above-mentioned methods of treatment or pharmaceutical compositions.

DETAILED DESCRIPTION OF THE INVENTION

The novel compounds of the present invention have structural Formula I:

(I)

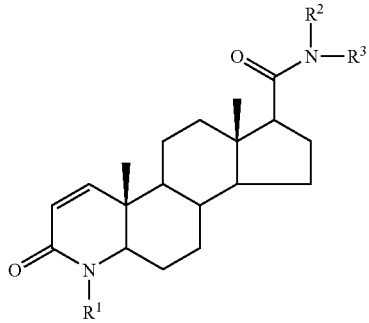

or a pharmaceutically acceptable salt or ester thereof, wherein:

$R^1$ is selected from methyl and ethyl;

$R^2$ is selected from (a) H, and (b) $C_{3-6}$ alkyl;

$R^3$ is selected from:

(a) diarylmethyl, either unsubstituted or substituted on one or both of the aryl ringses with one to three substituents independently selected from:

(1) halo (F, Cl, Br, I), (2) $C_{1-2}$ alkyl;

(3) trifluoromethyl, (4) nitro, (5) hydroxy, (6) cyano, (7) phenyl, (8) $C_{1-2}$ alkyloxy, (9) heteroaryl,

(10) $S(O)_nR^4$, wherein n is selected from 0, 1, and 2, and

(11) alkyoxy;

(b) phenyl substituted with one to three substituents independently selected from:

(1) halo (F, Cl, Br, I), (2) $C_{1-2}$ alkyl;

(3) trifluoromethyl, (4) nitro, (5) hydroxy, (6) cyano, (7) phenyl, (8) $C_{1-2}$ alkyloxy, (9) heteroaryl,

(10) $S(O)_nR^4$, wherein n is selected from 0, 1, and 2, and

(11) alkyoxy;

(c) heteroaryl, either unsubstituted or substituted with one to three substituents independently selected from:

(1) halo (F, Cl, Br, I), (2) $C_{1-2}$ alkyl;

(3) trifluoromethyl, (4) nitro, (5) hydroxy, (6) cyano, (7) amino, (8) $C_{1-2}$ alkyloxy, (9) phenyls, and

(10) heteroaryl;

(d) naphthyl, either unsubstituted or substituted with one to three substituents independently selected from:

(1) halo (F, Cl, Br, I),
(2) $C_{1-2}$ alkyl;
(3) trifluoromethyl,
(4) nitro,
(5) hydroxy,
(6) cyano,
(7) amino,
(8) $C_{1-2}$ alkyloxy, and
(9) $S(O)_nR^4$, wherein n is selected from 0, 1, and 2; and $R^4$ is selected from:
(a) $C_{1-4}$ alkyl,
(b) phenyl, and
(c) heteroaryl.

Combinations of substituents and/or variables are [pennisible] *permissible* only if such combinations result in stable compounds.

In one embodiment of the instant invention are compounds of Formula I wherein $R^3$ is diarylmethyl, either unsubstituted or substituted on an aryl moiety with one to three substituents independently selected from (1) halo (F, Cl, Br, I),
(2) $C_{1-2}$ alkyl;
(3) trifluoromethyl,
(4) nitro,
(5) hydroxy
(6) cyano,
(7) phenyl,
(8) $C_{1-2}$ alkyloxy,
(9) heteroaryl,
(10) $S(O)_nR^4$, wherein n is selected from 0, 1, and 2, and
(11) alkyoxy.

In one class of this embodiment are compounds wherein $R^3$ is unsubstituted diphenylmethyl.

In one subclass of this class are compounds wherein $R^2$is methyl.

Examples of compounds of this subclass exhibiting both 5α-reductase type 1 and type 2 inhibitory and androgen receptor antagonistic activity are:

N-(diphenylmethyl)-4-methyl-3-oxo-4-aza-5α-androst-1-ene-17β-carboxamide;

N-(diphenylmethyl)-N-methyls-4-methyl-3-oxo-4-aza-5α-androst-1-ene-17β-carboxamide.

In another embodiment of the present invention are compounds of Formula I wherein $R^3$ is phenyl substituted with one to three substituents independently selected from (1) halo, (F, Cl, Br, I),
(2) $C_{1-2}$ alkyl;
(3) trifluoromethyl,
(4) nitro,
(5) hydroxy,
(6) cyano,
(7) phenyl,
(8) $C_{1-2}$ alkyloxy,
(9) heteroaryl,
(10) $S(O)_nR^4$, wherein n is selected from 0, 1, and 2, and
(11) alkyoxy;

In one class of this embodiment $R^1$ is methyl.

Examples of compounds exhibiting both 5α-reductase type 1 and type 2 inhibitory and androgen receptor antagonistic activity of this class are:

N-(2-methylphenyl)-3-oxo-4-aza-4-methyl-5α-androst-1-ene-17β-carboxamide;

N-(2-methoxyphenyl)-3-oxo-4-aza-4-methyl-5α-androst-1-ene-17β-carboxamide;

N-(2-chlorophenyl)-3-oxo-4-aza-4-methyl-5α-androst-1-ene-17β-carboxamide;

N-(4-chlorophenyl)-3-oxo-4-aza-4-methyl-5α-androst-1-ene-17β-carboxamide;

N-(2-fluorophenyl)-3-oxo-4-aza-4-methyl-5α-androst-1-ene-17β-carboxamide;

N-(2-trifluoromethyl-phenyl)-3-oxo-4-aza-4-methyl-5α-androst-1-ene-17β-carboxamide;

N-(2,5-bistrifluoromethyl-phenyl)-3-oxo-4-aza-4-methyl-5α-androst-1-ene-17β-carboxamide;

N-(2-biphenyl)-3-oxo-4-aza-4-methyl-5α-androst-1-ene-17β-carboxamide;

N-(4-biphenyl)-3-oxo-4-aza-4-methyl-5α-androst-1-ene-17β-carboxamide;

In another embodiment of the present invention, $R^3$ is heteroaryl, either unsubstituted or substituted with one to three substituents independently selected from:

(1) halo (F, Cl, Br, I),
(2) $C_{1-2}$ alkyl;
(3) trifluoromethyl,
(4) nitro,
(5) hydroxy,
(6) cyano,
(7) amino,
(8) $C_{1-2}$ alkyloxy,
(9) phenyl, and
(10) heteroaryl;

In one class of this embodiment heteroaryl is pyridyl pyrazinyl pyrazolyl, or thiazolyl.

Examples of compounds of this class are:

N-(4-pyridyl)-3-oxo-4-methyl-4-aza-5α-androst-1-ene-17β-carboxamide,

N-(3-pyridyl)-3-oxo-4-methyl-4-aza-5α-androst-1-ene-17β-carboxamide,

N-(pyrazinyl)-3-oxo-4-methyl-4-aza-5α-androst-1-ene-17β-carboxamide,

N-(3-pyrazoyl)-3-oxo-4-methyl-4-aza-5α-androst-1-ene-17β-carboxamide, and

N-(2-thiazolyl)-3-oxo-4-aza-4-methyl-5α-androst-1-ene-17β-carboxamide.

In another embodiment of the present invention, $R^3$ is naphthyl, either unsubstituted or substituted with one to three substituents independently selected from:

(1) halo (F, Cl, Br, I),
(2) $C_{1-2}$ alkyl;
(3) trifluoromethyl,
(4) nitro,
(5) hydroxy,
(6) cyano,
(7) amino,
(8) $C_{1-2}$ alkyloxy, and
(9) $S(O)_nR^4$, wherein n is selected from 0, 1, and 2.

In one class of this embodiment, $R^3$ is unsubstituted naphthyl.

Examples of compounds of this class include:

N-(2-naphthyl)-3-oxo-4-aza-4-methyl-5α-androst-1-ene-17β-carboxamide, and

N-(1-naphthyl)-3-oxo-4-aza-4-methyl-5α-androst-1-ene-17β-carboxamide,

As used herein "alkyd" is intended to include both branched- and straight-chain saturated aliphatic hydrocarbon groups having the specified number of carbon atoms, e.g., methyl (Me). ethyl (Et), propyls, butyl, pentyl, hexyls, heptyl, octyls, nonanyl, decyl, undecyl, dodecyl, and the isomers thereof such as isopropyl (i-Pr), isobutyl (i-Bu), secbutyl (s-Bu), tertbutyl (t-Bu), isopentane, isohexane, etc. "Alkyloxy" (or "alkoxy") represents an alkyl group having the indicated number of carbon atoms attached through an oxygen bridge, e.g., methoxy, ethoxy, propyloxy, isopropxy, n-butoxy, iso-butoxy, sec-butoxy, t-butoxy and the like.

As used herein "aryl" is intended to include: phenyl and naphthyl; and "heteroaryl" is intended to include: pyridyl, furyl, pyrryl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl, and benzoxazolyl. Preferably, "heteroaryl" represents pyridyl, pyrazinyl, pyrazolyl, and thiazolyl. The heteroaryl ring may be substituted, or attached within structural formula I, at any heteroatom (N, O and S) or carbon atom in the ring which results in the creation of a stable, uncharged structure.

Also included within the scope of this invention are pharmaceutically acceptable salts of the compounds of formula I, where a basic or acidic group is present on the structure. Where a basic group is present, such as amino, and acidic salt, i.e., hydrochloride, hydrobromide, acetate, pamoate, and the like, can be used as the dosage form. Representative salts include the following salts: acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromides, tannate, hydrochloride, tartrates, hydroxynaphthoate, teoclate, iodide, tosylate, isothionate, triethiodide, lactate, and valerate.

The compounds of the present invention may have chiral centers other than those centers whose stereochemistry is depicted in Formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "therapeutically effective amount" means that amount of a drug or pharmaceutical agent that will elicit the biological or medical response of a tissue, system, animal or human that is being sought by a researcher, veterinarian, medical doctor or other clinician, which includes alleviation of the symptoms of the disorder being treated. The novel methods of treatment of this invention are for disorders known to those skilled in the art. The term "mammal" includes humans.

The present invention has the objective of providing methods of treating hyperandrogenic conditions including androgenic alopecia, male pattern baldness, acne vulgaris, seborrhea, and female hirsutism by oral, systemic, parenteral or topical administration of the novel compounds of formula I either alone or in combination with a 5α-reductase 2 inhibitor, or a potassium channel opener, or a retinoic acid or derivative thereof. Alternatively, treatment may encompass administration of a combination of a compound of Formula I with a 5α-reductase 2 inhibitor and another active agent such as a potassium channel opener, or a retinoic acid or derivative thereof. The term "treating androgenic alopecia" is intended to include the arresting and/or reversing of androgenic alopecia, and the promotion of hair growth.

The present invention has the further objective of providing methods of treating benign prostatic hyperplasia, prostatis, and treating and/or preventing prostatic carcinoma by oral, systemic or parenteral administration of the novel compounds of formula I either alone or in combination with a 5α-reductase 2 inhibitor. Alternatively, treatment may encompass administration of a combination of a compound of formula I with a 5α-reductase 2 inhibitor and another active agent such as an α1 or an $\alpha 1_{\alpha}$ adrenergic receptor antagonist.

The present invention also has the objective of providing suitable topical, oral, systemic and parenteral pharmaceutical formations for use in the novel methods of treatment of the present invention. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release (formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an antiandrogenic agent.

The daily dosage of the products may be varied over a range from 0.01 to 1,000 mg per adult human/per day. For oral administration, the compositions are preferably provided in the form of tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg/kg to about 50 [mgas/g] *mg/kg* of body weight per day. The range is more particularly from about 0.001 [msg/kg] *mg/kg* to 7 mg/kg of body weight per day.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

For the treatment of androgenic alopecia, male pattern baldness, acne vulgaris, seborrhea, and female hirsutism, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. These topical pharmaceutical compositions containing the compounds of the present invention ordinarily include about 0.005% to 5% by weight of the active compound in admixture with a pharmaceutically acceptable vehicle.

For the treatment of acne vulgaris, androgenic alopecia, male pattern baldness, seborrhea, female hirsutism, benign prostatic hyperplasia, prostatitis and the prevention and/or treatment of prostatic cancer, the compounds of the instant invention can be combined with a therapeutically effective amount of another 5α-reductase inhibitor, such as finasteride, or other 5α-reductase inhibitor compounds having type 2 activity or dual activity for both isozymes, in a single oral, systemic, or parenteral pharmaceutical dosage formulation. Alternatively, a combined therapy can be employed wherein the compound of formula I and the other 5α-reductase inhibitor are administered in separate orals, systemics, or parental dosage formulations. Also, for the skin and scalp related disorders of acne vulgaris, androgenic alopecia, male pattern baldness, seborrhea, and female hirsutism, the compounds of the instant invention and another 5α-reductase inhibitor such as finasteride can be formulated for topical administration. For examples, a compound of formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of Formula I.

Furthermore, administration of a compound of the present invention in combination with a therapeutically effective amount of a potassium channel opener, such as minoxidil, cromakalin, pinacidil, a compound selected from the classes of S-triazine, thiane-1-oxide, benzopyran, and pyridinopyran derivatives or a pharmaceutically acceptable salt thereof, ran derivatives or a pharmaceutically acceptable salt thereof, may be used for the treatment of androgenic alopecia including male pattern baldness. Therapy may further comprise the administration of a 5α-reductase type 2 inhibitor such as finasteride, or a type 1 and type 2 dual inhibitor, in combination with a compound of the present invention and a potassium channel opener such as minoxidil. The active agents can be administered in a single topical dosage formulation, or each active agent can be administered in a separate dosage formulation, e.g., in separate topical dosage formulations, or an oral dosage formulation of a compound of formula I in combination with a topical dosage formulation of, e.g., minoxidil, or a single oral dosage formulation of a compound of formula I and another 5α-reductase inhibitor, in combination with a topical dosage formulation of, e.g., minoxidil. See, e.g., U.S. Pat. Nos. 4,596,812, 4,139,619 and WO 92/02225, published Feb. 20, 1992, for dosages and formulations of calcium channel openers.

Furthermore, for the treatment of acne vulgaris, a combined therapy can be used by administering a therapeutically effective amount of a compound of formula I in combination with a therapeutically effective amount of retinoic acid or a derivative thereof, e.g., an ester or amide derivative thereof, such as e.g., tretinoin or isotretinoin. Optionally, this combined therapy for acne vulgaris may further include a 5α-reductase type 2 inhibitor such as finasteride, or a dual type 1 and type 2 inhibitory compound.

Also, for the treatment of benign prostatic hyperplasia, a combined therapy comprising a administration of a compound of formula I with a 5α-reductase type 2 inhibitor, such as e.g., finasteride, and an alpha-1 adrenergic receptor antagonist, such as e.g., terazosin, doxazosin, prazosin, bunazosin, indoramin or alfuzosin, may be employed. More particularly, the combined therapy can comprise administering a compound of formula I with a 5α-reductase type 2 inhibitor, such as e.g., finasteride, and an alpha-$1_\alpha$ adrenergic receptor antagonist. Compounds which are useful as alpha-$1_\alpha$ adrenergic receptor antagonists can be identified according to procedures known to those of ordinary skill in the art, for examples, as described in PCT/US93/09187 (W094/08040, published Apr. 14, 1994); PCT/US94/03852 (WO 94/22829, published Oct. 13, 1994); PCT/US94/10162 (WO 95/07075, published Mar. 16, 1995), and U.S. Pat. No. 5,403,847.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-celluose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotionss, and shampoos in cream or gel formulations. See, e.g. EP 0 285 382.

The compounds of the present invention can also be administered in the form of liposome delivery systems, such as small unilamellar vesicles, large unilamellare vesicles and multilamellar vesicles. Liposomes can be formed from a variety of phospholipids, such as cholesterol, stearylamine or phosphatidylcholines.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail.

Preparation of the starting material, methyl 4-methyl-3-oxo-4-aza-5α-androst-1-ene-17β-carboxylate, is known in the art and is described with particularly in Rasmusson et al., J. Med. Chem. 1986, vol. 29(11), pp. 2298–2315.

-continued

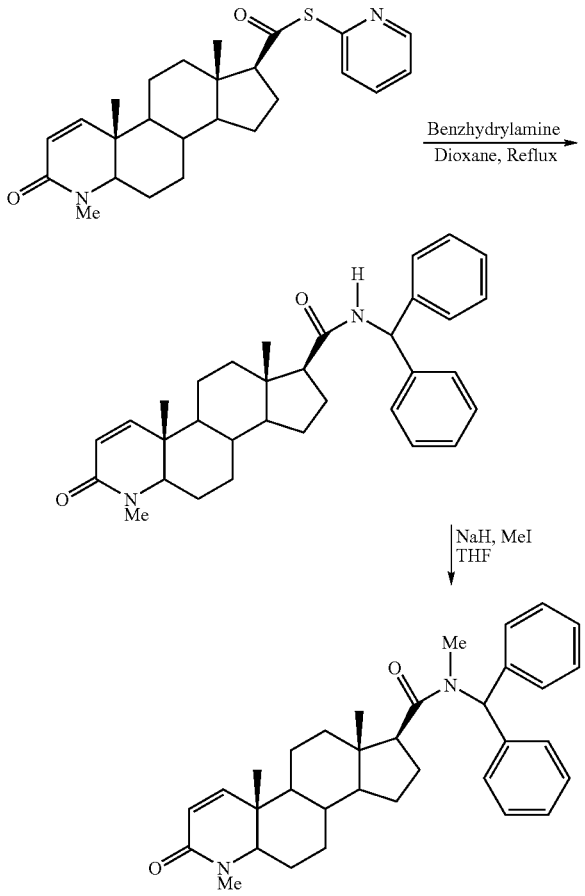

Scheme 1:
Synthesis of 4 N-methyl-3-oxo-5α-androst-1-ene-17β–N–diphenylmethyl carboxamides

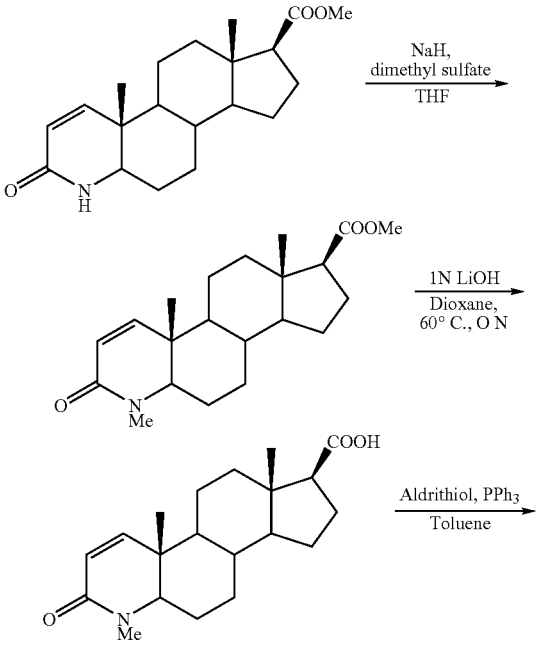

Scheme 2:
Synthesis of 4 N-methyl-3-oxo-5α-androst-1-ene-17β-N-aryl and heteroaryl carboxamides

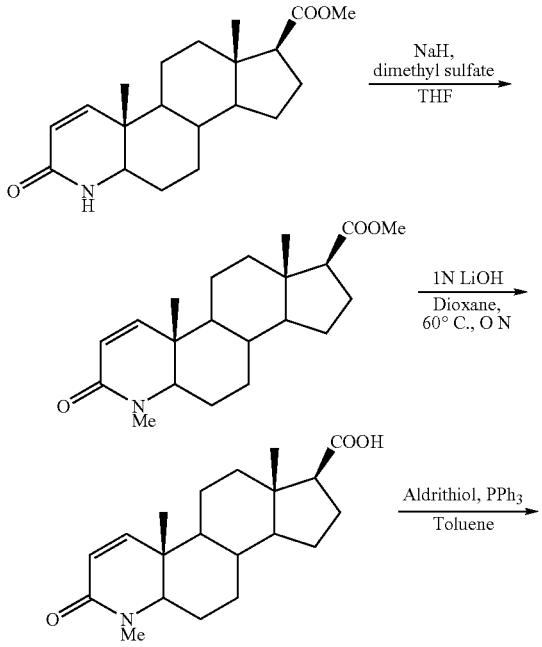

-continued

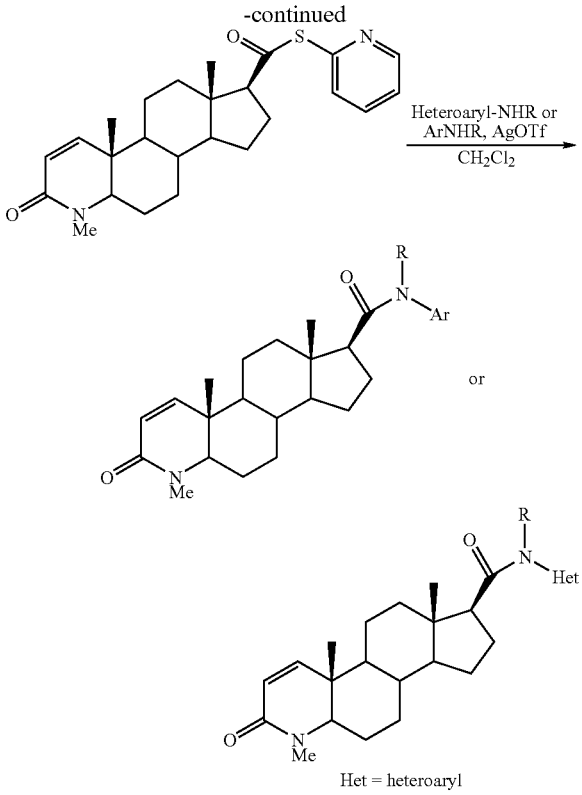

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

All temperatures given in the following examples are in degrees Celsius. "TLC" is thin layer chromatography, conducted on $SiO_2$ plates, unless specified otherwise.

EXAMPLE 1

N-(4-chlorophenyl)-3-oxo-4-methyl-4-aza-5α-androst-1-ene-17β-carboxamide

Step 1: Synthesis of 4-methyl-3-oxo-4-aza-5α-androst-1-ene-17β-methyl carboxylate To a suspension of sodium hydride (1.8 g, 45.25 mmoles) in tetrahydrofuran (100 mL) was added 3-oxo-4-aza-5α-androst-1-ene-17β-methyl carboxylate (10.0 g, 30.2 mmoles, see Rasmusson et al., J. Med. Chem. 1986, vol. 29(11), pp. 2298–2315 for details of preparation). After half an hour dimethyl sulfate (4.28 mL, 45.25 mmoles) was added and the reaction was stirred for 3 hours. The reaction was quenched with the addition of water and solvent was evaporated in vacuo. The residue was dissolved in methylene chloride (500 mL) and washed with water (250 mL) and brine (250 mL). The organic phase was dried over sodium sulfate and filtered. The solvent was evaporated in vacuo to yield the titled compound as a yellow oil. The compound was taken on to the next step without further purification. TLC rf=0.6, 1:4 acetone-methylene chloride.

400 MHz $^1$H NMR ($CDCl_3$) δ8 0.65 (s, 3H); 2.93 (ss, 3H); 3.33 (dd, 1H); 3.65 (s, 3H); 5.83 (d, 1H); 6.67 (d, 1H).

Step 2: 4-methyl-3-oxo-4-aza-5α-androst-1-ene-17β-carboxylic acid

A mixture of dioxane (300 mL), 1M lithium hydroxide solution (100 mL) and 4-methyl-3-oxo-4-aza-5α-androst-1-ene-17β-methyl carboxylate (11.3 g.) was refluxed at 110° C. for 24 hours. The reaction was cooled and acidified with 1M hydrochloric acid. Acetone (200 mL) was added and solution was filtered, the solid was washed with cold acetone (100 mL). The solid was dried under vacuo for 2 hours to yield the titled compound. No further purification was done. TLC rf=0.0, 1:4 acetone-methylene chloride.

400 MHz $^1$H NMR ($CDCl_3$) δ0.73 (s, 3H); 0.995 (s, 3H); 2.94 (s, 3H); 3.33 (dd, 1H); 5.85 (d, 1H); 6.68 (d, 1H).

Step 3: 4-methyl-3-oxo-4-aza-5α-androst-1-ene-17β-(2-thiopyridine) carboxylate

A mixture of 4-methyl-3-oxo-4-aza-5α-androst-1-ene-17β-methyl carboxylate (9.3 g, 0.0278 moles), 2-Aldrithiol™ (2,2'-dithiodipyridine, 12.25 g, 0.0556 moles), triphenyl phosphine (14.58 g, 0.0556 moles) and toluene (60.0 mL) was stirred overnight at room temperature under a nitrogen atmosphere. The reaction was filtered to give a yellow/white solid (12.0 g.). The solid was triturated in ethyl ether (250 mL) to yield the titled compound as a white solid. No further purification was done. TLC rf=48, 1:9 acetone-methylene chloride.

400 MHz $^1$H NMR ($CDCl_3$) δ0.74 (s, 3H); 0.90 (s, 3H); 2.93 (s, 3H); 3.34 (dd, 1H); 5.84 (d, 1H); 6.68 (d, 1H).

Step 4: N-(4-chlorophenyl)-3-oxo-4-methyl-4-aza-5α-androst-1-ene-17β-carboxamide A mixture of 4-methyl-3-oxo-4-aza-5α-androst-1-ene-17β-(2-thiopyridine) carboxylate (200 mg.s. 0.47 mmoles), silvertriflate (121 msg, 0.47 mmoles), p-chloroamiline (180 mg., 1.41 mmoles) and toluene (4.0 mL) was stirred overnight. The reaction was then filtered and the filtrate was diluted with ethylacetate (100 mL). The organic phase was washed with 1M hydrochloric acid (100 mL) and brine (100 mL). The organic phase was dried over sodium sulfate and filtered. The solvent was evaporated in vacuo to give a dark yellow foam. The crude was chromatographed on preparative TLC plates (SiO2) using 1:9 acetone/methylene chloride as the mobile phase to yield the titled compound as a white foam. TLC rf=0.5, 1:9 acetone-methylene chloride.

400 MHz $^1$H NMR ($CDCl_3$) δ0.75 (s, 3H); 0.90 (s, 3H); 2.94 (s, 3H); 3.34 (dd, 1H): 5.58 (d, 1H); 6.66 (d, 1H).

EXAMPLES 2–9

The following compounds were obtained following the procedure of Example 1 and employing the appropriate arylamines.

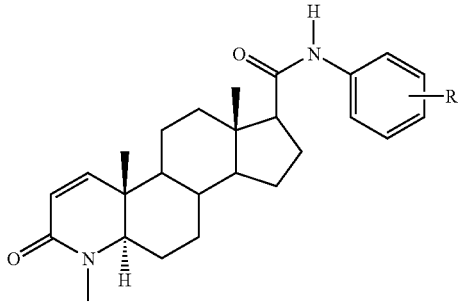

400 MHZ, $^1$H-NMR (δ ppm) $CDCl_3$

| Ex. No. | R | $C_{18}$ | $C_{19}$ | $C_5$ | $NCH_3$ | $\Delta^2$ | other | Mass spec |
|---|---|---|---|---|---|---|---|---|
| 2 | 2-OMe | 0.74s | 0.92s | 3.34m | 2.94s | 5.84d 6.68d | 3.87s (OMe) | 437 (M + 1) |
| 3 | 2-F | 0.74s | 0.90s | 3.34m | 2.93s | 5.50d 6.67d | | 425 (M + 1) |
| 4 | 2-$CF_3$ | 0.77s | 0.91s | 3.35m | 2.94s | 5.84d 6.77d | | 475 (M + 1) |
| 5 | 2-Me | 0.79s | 0.91s | 3.35m | 2.94s | 5.85d 6.67d | 2.24s (2-Me) | 421 (M + 1) |
| 6 | 2-Cl | 0.75s | 0.91s | 3.34m | 2.94s | 5.84d 6.68d | | 441 (M + 1) |
| 7 | 2,5-bis $CF_3$ | 0.77s | 0.91s | 3.34m | 2.94s | 5.84d 6.67d | | 543 (M + 1) |
| 8 | 2-phenyl | 0.62s | 0.87s | 3.30m | 2.92s | 5.86d 6.65d | | 483 (M + 1) |
| 9 | 4-phenyl | 0.78s | 0.91s | 3.35m | 2.94s | 5.86d 6.67d | | 483 (M + 1) |

EXAMPLE 10

N-(diphenylmethyl)-4-methyl-3-oxo-4-aza-5α-androst-1-ene-17-β-carboxamide

A mixture of 4-methyl-3-oxo-4-aza-5α-androst-1-ene-17β-(2-thiopyridine) carboxylate (200 mg, 0.47 mmoles the product of Example 1, Step 3), aminodiphenylmethane (256 mg, 1.41 mmoles) and dioxane (4.0 mL) was refluxed overnight. The reaction was diluted with ethyl acetate (100 mL). The organic phase was washed with 1M hydrochloric acid (100 mL) and brine (100 mL). The organic phase was dried over sodium sulfate and filtered. The solvent was evaporated in vacuo to give a yellow foam. The crude product was chromatographed on preparative TLC plates ($SiO_2$) using 1:9 acetone/methylene chloride as the mobile phase to yield the titled compound as a white foam. TLC rf=0.5, 1:9 acetone-methylene chloride. 400 MHz $^1$H NMR ($CDCl_3$) δ0.67 (s, 3H); 0.89 (s, 3H); 2.93 (s, 3H); 3.32 (dd, 1H); 5.80 (d, 1H); 5.85 (d, 1H); 6.23 (d, 1H); 6.62 (d, 1H).

EXAMPLE 11

N-(diphenylmethyl)-N-(methyl)-4-methyl-3-oxo4-aza-5α-androst-1-ene-17-β-carboxamide To mixture of N-(diphenylmethyl)-4-methyl-3-oxo-4-axa-5α-androst-1-ene-17-β,-carboxamide (obtain via the procedures of Example 8, 100 mg, 0.20 mmoles), sodium hydride (8.8 mg, 0.22 mmoles) and tetrahydrofuran (2.0 mL) was added [jodomethane] *iodomethane* (0.0138 mL, 0.22 mmoles). The reaction was stirred overnight. The reaction was quenched with water and the solvent was evaporated in vacuo. The residue was dissolved in methylene chloride (75 mL) and washed with water (50 mL) and brine (50 mL). The organic phase was dried over sodium sulfate and filtered. The solvent was evaporated in vacuo to give a yellow/white foam. The crude foam was chromatographed on preparative TLC plates ($SiO_2$) using 1:9 acetone:methylene chloride as the mobile phase to yield the titled compound as a white foam. TLC rf=0.6, 1:9 acetone:methylene chloride.

400 MHz $^1$H NMR ($CDCl_3$) δ8 0.83 (s, 3H); 0.92(s, 3H); 2.84 (s, 3H); 2.95 (s, 3H); 3.34 (dd, 1H); 5.84 (d, 1H); 6.64 (d, 1H).

EXAMPLES 12–18

The following compounds were obtained following the procedure of Example 1 and employing the appropriate heteroarylamines of arylamines.

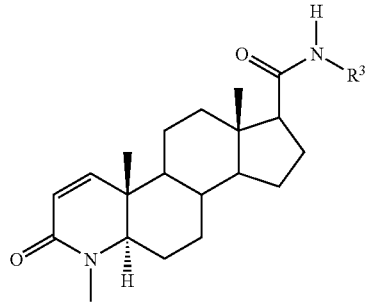

400 MHZ, $^1$H-NMR (δ ppm) $CDCl_3$

| Ex. No. | $R^3$ | $C_{18}$ | $C_{19}$ | $C_5$ | $NCH_3$ | $\Delta^2$ | other | Mass spec |
|---|---|---|---|---|---|---|---|---|
| 12 | 4-pyridyl | 0.75s | 0.90s | 3.33m | 2.94s | 5.85d 6.66d | | 2408 (M + 1) |
| 13 | 3-pyridyl | 0.76s | 0.91s | 3.34m | 2.94s | 5.85d 6.67d | | 408 (M + 1) |
| 14 | pyrazine | 0.76s | 0.91s | 3.34m | 2.94s | 5.85d 6.66d | | 409 (M + 1) |
| 15 | 3-pyrazole | 0.76s | 0.89s | 3.33m | 2.94s | 5.83d 6.65d | | 397 (M + 1) |
| 16 | 2-thiazole | 0.73s | 0.90s | 3.34m | 2.93s | 5.84d 6.65d | | 414 (M + 1) |
| 17 | 2-naphthyl | 0.80s | 0.91s | 3.36m | 2.95s | 5.89d 6.69d | | 457 (M + 1) |
| 18 | 1-naphthyl | 0.85s | 0.94s | 3.35m | 2.96s | 5.85d 6.69d | | 457 (M + 1) |

Biological Assays

Preparation of Human Prostatic and Scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethyl-sulfonyl fluoride, 1 mM dithiothreitol (DTT) containing 0.25 M sucrose using a Potter-Elvehjem homogenizer. A crude nuclear pellet was prepared by centrifugation of the homogenate at 1,500× G for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase Assay

The reaction mixture for the type 1 5α-reductase contained 40 mM potassium phosphate, pH 6.5, 5 mM [7-$^3$H]-testosterone, 1 mM dithiothreitol and 500 μM NADPH in a final volume of 100 μL. The reaction mixture for the type 2 5α-reductase contained 40 mM sodium citrate, pH 5.5 0.3 mM [7-$^3$H]-testosterone, 1 mM dithiothreitol and 500 μM NADPH in a final volume of 100 μL. Typically, the assay was initiated by the addition of 50–100 μg prostatic homogenate or 75–200 μg scalp homogenate and incubated at 37° C. After 10–50 min. the reaction was quenched by extraction with 250 μL of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column established in 1 ml/min 70% cyclohexane: 30% ethyl acetate; retention times: DHT, 6.8–7.2 min.; androstanediol, 7.6–8.0 min.; T, 9.1–9.7 min.). The HPLC system consisted of a Waters Model 680 Gradient System equipped with a Hitachi Model 655α autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition Studies

Compounds were dissolved in 100% ethanol. The compound to be tested was pre-incubated with the enzyme (either 5α-reductase type 1 or 2) prior to initiation by addition of substrate testosterone. $IC_{50}$ values represent the concentration of inhibitor required to decrease enzyme conversion of testosterone to dihydrotestosterone by 50% of the control. $IC_{50}$ values were determined using a 6 point titration where the concentration of the inhibitor was varied from 0.1 to 1000 nM. Representative compounds of this invention were tested in the above described assay for 5α-reductase type 1 and type 2 inhibition.

Human Dermal Papilla Cell Assay

The dermal papilla is a small group of cells at the base of each hair follicle, and it is presently thought that these cells are stem cells form the basis for hair growth. These cells have been shown to have 5α reductase activity and it is therefore possible to test inhibitors of 5α reductase in these cell culture systems.

Isolated and cultured dermal papilla cells are prepared according to the methods of Messenger A. G. "The Culture of Dernmal Papilla Cells From Human Hair Follicles," Br. J. Deimatol., 110:685–689 (1984) and Itami, S. et al., "5α-Reductase Activity In Cultured Human Dermal Papilla Cells From Beard Compared With Reticular Dermal Fibroblasts," J. Invest. Dermatol., 94:150–152 (1990). Beard dermal papilla cells and occipital scalp hair of two different individuals are used throughout the study. All experiments are performed at confluency after the fourth to sixth subculture. Confluent monolayers are rinsed with phosphate-buffered saline, scraped from dishes by rubber policemen, and collected into a centrifuge tube. The cell suspensions are centrifuged at 1,500 rpm for 10 min. at 4° C. The pellets are resuspended in 20 mM Tris-HCl buffer, pH 7.5, at 4° C., containing 250 mM sucrose, 1 mM $MgCl_2$, and 2 mM $CaCl_2$, by vortexing and 10 passes through a 25-gauge needle. The crude homogenate is further homogenized by a teflon-glass homogenizer, and is used as the cell homogenate. For the study of subcellular localization of 5α-reductase, the cell homogenate is centrifuged at 800× g for 10 min. to yield a crude nuclear pellet. The resultant supernatant is centrifuged at 10,000× g for 15 min. to produce a crude mitochondrial pellet. The supernatant is centrifuged at 100,000× g for 60 min. to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 ml of the cell homogenate, in a final volume of 100 ml. Each tube contains 50–100 mg of cellular protein. Incubation is carried out at 37° C. for 30 min. During this incubation, the reaction is proportional to the time. For the study the optimum pH, citrate buffer is used at pH 4.5–6.5, and the Tris HCl buffer at pH 7.0–9.0. The protein content is determined by the method of Lowry, et al., "Protein Measurement With The Folin Phenol Reagent," J. Biol. Chem., 193:265–275 (1951).

After incubation, the reaction is stopped by adding 4 times volume of chloroform-methanol (2/1: V/V) containing 110 mg each of carrier steroids. The extracted steroids are analyzed by thin-layer chromatography as previously described by Gomez, et al.; "In Vitro Metabolism Of Testosterone-4-$^{34}$C and D-androstene-3, 17-dione-4$^{14}$C In Human Skin.," Biochem., 7:24–32 (1968), and the purity of each steroid is determined by the recrystallization method. The activity of 5α-reductase is expressed by the sum of dihydro-osterone, androstanediol and androstanedione formed. [1,2-$^3$H]-osterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaza, Kans.). All other chemicals are of reagent grade.

An assay for the detection of human androgen receptor activity is described in Tillie, W. D. et al. PNAS (USA) 1989, volume 86, p. 327.

Reductase (5aR) Activities and Anti-Androgen Activity (hAR) of compounds of the present invention are illustrated in the table below:

| Ex | | | $IC_{50}$ (nM, human) | | |
|---|---|---|---|---|---|
| No. | $R^3$ | $R^2$ | Type 1 5aR | Type 2 5aR | hAR |
| 1 | 4-chlorophenyl | H | 40 | 100 | 10 |
| 2 | 2-methoxyphenyl | H | 20 | 100 | 40 |
| 3 | 2-fluorophenyl | H | 20 | 60 | 9 |
| 4 | 2-$CF_3$-phenyl | H | 2 | 7 | 30 |
| 5 | 2-methylphenyl | H | 20 | 20 | 30 |
| 6 | 2-chlorophenyl | H | 6 | 10 | 8 |
| 7 | 2.5-bis$CF_3$-phenyl | H | 4 | 20 | 20 |
| 10 | diphenylmethyl | H | 20 | 2 | 40 |
| 11 | diphenylmethyl | $CH_3$ | 3 | 0.3 | 850 |

The following describes an example of methodology that can be used for detection of hair growth.

MACROPHOTOGRAPHY AND GLOBAL PHOTOGRAPHY PROCEDURE FOR DETECTION OF HAIR GROWTH

A. Macrophotographic Procedure

| | |
|---|---|
| Location: | ID card<br>Haircount target area |
| Equipment: | Film: Kodak-T-max 24 exposure each of same emulsion lot number |
| Camera: | Nikon N-6000 |
| Lens: | Nikkor 60 mm f2.8 |
| Flashes: | Nikon SB-21B Macroflash |
| Device: | registration device |

Photographic Procedure:

In these clinical photographs, the only variable allowed is the haircount. Film emulsion, lighting, framing, exposure, and reproduction ratios are held constant.

1. The haircount area on the patient is prepared as follows: A small (~1 mm) dot tatoo is placed at the beginning of the study at the leading edge of the bald area directly anterior to the center of the vertex bald spot, using a commercial tattooing machine or manually (needle and ink). An area approximately one square inch in size, centered at the tattoo at the leading edge of the balding area, is clipped short (~2 mm). Cut hairs are removed from the area to be photographeds, using tape. Compressed air and/or ethanol wipes may also be used to facilitate removal of cut hairs.

2. Magnification: Each lens supplied has a fixed reproduction ratio of 1:1.2.

Aperture: Every photograph is taken at f/22.

Film: T-Max 100 (24 exposure) is used.

3. Patient's haircount target area. Three exposures (−2/3, 0, and +2/3 f-stop).

A trained technician places a transparency over the photographic print and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E. A. and DeLong E., J. American Academy of Dermatology, Vol. 23, p. 470 (1990).

B. Global Photographic Procedure

| | |
|---|---|
| Locations: | Color card/patient Id<br>Global photograph |
| Equipment: | Film: Kodachrome KR-64 24 exposure each of same emulsion lot number |
| Camera: | Nikon N-6000 |
| Lens: | Nikkor 60 mm f2.8 |
| Flashes: | Nikon SB-23 |

Photographic Procedure

In these clinical [photographss] *photographs*, the only variable allowed is the global area's appearance. Anything extraneous to the area (clothing, furnitures, walls, etc.) is eliminated from the fields to be photographed.

1. Patients will have global photographs taken prior to hair clipping with the head in a fixed position (determined by the supplied stereotactic device). Hair on the patient's head is positioned consistently so as to not obscure the bald area.

2. Magnification: Each lens supplied has a fixed reproduction ratio of 1:6.

Aperture: Every photograph will be taken at f11.

Film: Kodachrome (24 exposure) is used.

3. Patient's global photographs. Three exposures at zero compensation.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

[1. A compound of structural formula I:

(I)

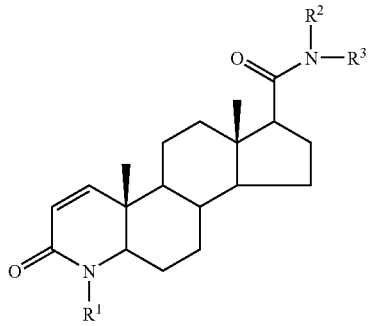

or a pharmaceutically acceptable salt or ester thereof, wherein:

$R^1$ is selected from methyl and ethyl;

$R^2$ is selected from:

(a) H, and (b) $C_{1-6}$ alkyl;

$R^3$ is heteroaryl, either unsubstituted or substituted with one to three substituents independently selected from:

(1) halo (F, Cl, Br, I), (2) $C_{1-2}$ alkyl;

(3) trifluoromethyl, (4) nitro, (5) hydroxy, (6) cyano, (7) amino, (8) $C_{1-2}$ alkyloxy, (9) phenyl, and

(10) heteroaryl; and $R^4$ selected from:

(a) $C_{1-4}$ alkyl, (b) phenyl, and (c) heteroaryl.]

[2. The compound according to claim 1 wherein $R^1$ is methyl.]

[3. The compound according to claim 2 wherein $R^2$ is selected from (a) H, and (b) methyl.]

[4. The compound according to claim 3 wherein heteroaryl is selected from:

(a) pyridyl, (b) pyrazinyl, (c) pyrazolyl, and (d) thiazolyl;

either unsubstituted or substituted with one to three substituents independently selected from:

(1) halo, (2) $C_{1-2}$ alkyl, (3) trifluoromethyl, (4) nitro, (5) hydroxy, (6) cyano, (7) amino, and (8) $C_{1-2}$ alkyloxy.]

[5. The compound according to claim 3 selected from:

(a) N-(4-pyridyl)-3-oxo-4-methyl-4-aza-5α-androst-1-ene-17β-carboxamide, (b) N-(3-pyridyl)-3-oxo-4-methyl-4-aza-5α-androst-1-ene-17β-carboxamide, (c) N-(pyrazinyl)-3-oxo-4-methyl-4-aza-5α-androst-1-ene-17β-carboxamide, (d) N-(3-pyrazoyl)-3-oxo-4-methyl-4-aza-5α-androst-1-ene-17β-carboxamide, (e) N-(2-thiazolyl)-3-oxo-4-aza-4-methyl-5α-androst-1-ene-17β-carboxamide.]

[6. A method of treating prostatic cancer in a human being in need of such treatment, comprising administering a therapeutically effective amount of the compound according to claim 1.]

[7. A method of treating prostatic cancer in a human being in need of such treatment, comprising administering a therapeutically effective amount of the compound according to claim 5.]

[8. A method of inhibiting 5α-reductase type 1, 5α-reductase type 2 and the human androgen receptor in a human in need of such inhibition by administering 0.01 to 1,000 mg per day of a compound according to claim 1.]

[9. The method according to claim 8 of inhibiting 5α-reductase type 1, 5α-reductase type 2 and the human androgen receptor in a human in need of such inhibition by administering 0.001 mg/kg to 7 mg/kg per day of a compound selected from:

(a) N-(4-pyridyl)-3-oxo-4-methyl-4-aza-5α-androst-1-ene-17β-carboxamide, (b) N-(3-pyridyl)-3-oxo-4-methyl-4-aza-5α-androst-1-ene-17β-carboxamide, (c) N-(pyrazinyl)-3-oxo-4-methyl-4-aza-5α-androst-1-ene-17β-carboxamide, (d) N-(3-pyrazoyl)-3-oxo-4-methyl-4-aza-5α-androst-1-ene-17β-carboxamide, (e) N-(2-thiazolyl)-3-oxo-4-aza-4-methyl-5α-androst-1-ene-17β-carboxamide.]

[10. A method of inhibiting 5α-reductase type 1, 5α-reductase type 2 and the human androgen receptor in a human in need of such inhibition by administering 0.01 to 1,000 mg per day of a compound selected from:

(a) N-(4-pyridyl)-3-oxo-4-methyl-4-aza-5α-androst-1-ene-17β-carboxamide, (b) N-(3-pyridyl)-3-oxo-4-methyl-4-aza-5α-androst-1-ene-18β-carboxamide, (c) N-(pyrazinyl)-3-oxo-4methyl-4-aza-5α-androst-1-ene-17β-carboxamide, (d) N-(3-pyrazoyl)-3-oxo-4-methyl-4-aza-5α-androst-1-ene-17β-carboxamide, and (e) N-(2-thiazolyl)-3-oxo-4-aza-4-methyl-5α-androst-1-ene-17β-carboxamide.]

[11. A composition comprising a compound according to claim 1 and a pharmaceutically acceptable carrier.]

[12. The composition according to claim 11 adapted for oral administration.]

[13. The composition according to claim 11 wherein the compound is selected from:

(a) N-(4-pyridyl)-3-oxo-4-methyl-4-aza-5α-androst-1-ene-17β-carboxamide, (b) N-(3-pyridyl)-3-oxo-4-methyl-4-aza-5α-androst-1-ene-17β-carboxamide, (c) N-(pyrazinyl)-3-oxo-4-methyl-4-aza-5α-androst-1-ene-17β-carboxamide, (d) N-(3-pyrazoyl)-3-oxo-4-methyl-4-aza-5α-androst-1-ene-17β-carboxamide, and (e) N-(2-thiazolyl)-3-oxo-4-aza-4-methyl-5α-androst-1-ene-17β-carboxamide.]

*14. N-(2-trifluoromethyl-phenyl)-3-oxo-4-aza-4-methyl-5α-androst-1-ene-17β-carboxamide.*

*15. A composition comprising N-(2-trifluoromethyl-phenyl)-3-oxo-4-aza-4-methyl-5α-androst-1-ene-17β-carboxamide and a pharmaceutically acceptable carrier.*

* * * * *